(12) United States Patent
Zoghbi et al.

(10) Patent No.: US 6,437,139 B1
(45) Date of Patent: Aug. 20, 2002

(54) SYNTHESIS OF PHARMACEUTICALLY USEFUL PYRIDINE DERIVATIVES

(75) Inventors: Michel Zoghbi; Liquin Chen, both of Richmond Hill (CA)

(73) Assignee: PDi-Research Laboratories, Inc., Richmond Hill (CA)

( * ) Notice: Subject to any disclaimer, the term of this patent is extended or adjusted under 35 U.S.C. 154(b) by 0 days.

(21) Appl. No.: 09/582,345

(22) PCT Filed: Dec. 11, 1998

(86) PCT No.: PCT/CA98/01153

§ 371 (c)(1),
(2), (4) Date: Jun. 23, 2000

(87) PCT Pub. No.: WO99/33807

PCT Pub. Date: Jul. 8, 1999

Related U.S. Application Data

(63) Continuation-in-part of application No. 09/063,001, filed on Apr. 21, 1998, now Pat. No. 6,121,454.

(30) Foreign Application Priority Data

May 6, 1997 (CA) .............................................. 2204580
Dec. 24, 1997 (CA) .............................................. 2225863

(51) Int. Cl.[7] ...................... C07D 211/72; C07D 211/84

(52) U.S. Cl. ........................................ 546/298; 546/303

(58) Field of Search .................................. 546/298, 303

(56) References Cited

U.S. PATENT DOCUMENTS

| | | | |
|---|---|---|---|
| 3,519,717 A | 7/1970 | Symchowicz ................. | 514/354 |
| 4,544,750 A | 10/1985 | Brandstrom et al. ......... | 546/290 |
| 4,620,008 A | 10/1986 | Brandstrom et al. ..... | 546/273.7 |
| 4,672,125 A | 6/1987 | Gray et al. .................. | 546/345 |
| 5,061,805 A | 10/1991 | Goe ............................. | 546/349 |
| 5,066,810 A | 11/1991 | Baumann ..................... | 546/300 |
| 5,374,730 A | 12/1994 | Slemon et al. ............ | 546/273.7 |
| 5,386,032 A | 1/1995 | Brandstrom et al. ..... | 546/273.7 |
| 5,510,090 A | 4/1996 | Cuillerdier et al. ............. | 423/9 |
| 6,121,454 A | 9/2000 | Zoghbi et al. ............... | 546/245 |

FOREIGN PATENT DOCUMENTS

| | | |
|---|---|---|
| CA | 1127158 | 7/1982 |
| CA | 1234118 | 3/1988 |
| CA | 1263119 | 11/1989 |
| DE | 29611 A | 5/1965 |
| EP | 0 103553 A1 | 3/1984 |
| EP | 0 103 553 B1 | 3/1984 |
| EP | 0176308 A | 4/1986 |
| EP | 0226558 A | 6/1987 |
| EP | 0446961 A | 9/1991 |
| EP | 0 484 265 | 5/1992 |
| EP | 0533131 A | 3/1993 |

OTHER PUBLICATIONS

Chemical Abstracts, vol. 119 (21)ABST.No. 225,834(a) Nov. 22, 1993.

Brown, H.C., et al., "A Convenient Conversion of Carboxylic Acids into Aldehydes", *Synthesis*, 1979, pp. 704–705.

Brown, H.C., et al., "Forty Years of Hydride Reductions", *Tetrahedron*, 1979, vol. 35, pp. 567–607.

Brown, H.C., et al., "Selective Reductions. 30. Effect of Cation and Solvent on the Reactivity of Saline Borohydrides for Reduction of Carboxylic Esters. Improved Procedures for the Conversion of Esters to Alcohols by Metal Borohydrides", *J. Org. Chem.*, 1982, vol. 47, pp. 4702–4708.

Brown, M.S., et al., "The Reduction of Esters with Sodium Borohydride[1]", *J. Org. Chem.*, 1963, vol. 28, pp. 3261–3263.

Kanazawa, R., et al., "Modified Sodium Bis[2–methoxyethoxy]aluminum Hydride Reagents for the Partial Reduction of Lactones and Esters", *Synthesis*, 1976, pp. 526–527.

Kornet, M.J., "Phenylurethans of Pyrazolidinols and Piperidazinols as Anticonvulsants", *J. Heterocyclic Chem.*, 1990, vol. 27, pp. 2125–2127.

Prasad, A.S.B., et al., "Convenient Methods for the Reduction of Amides, Nitriles, Carboxylic Esters, Acids and Hydroboration of Alkenes Using $NaBH_4/I_2$ System", *Tetrahedron*, 1992, vol. 48, No. 22, pp. 4623–4628.

Spinner, E. et al., "A Convenient Preparation of 4–Methoxypyridine", *Chemistry & Industry*, 1967, p. 1784.

Winterfeldt, E., "Applications of Diisobutylaluminum Hydride (DIBAH) and Triisobutylaluminium (TIBA) as Reducing Agents in Organic Synthesis", *Synthesis*, 1975, pp. 617–630.

(List continued on next page.)

*Primary Examiner*—Alan L. Rotman
*Assistant Examiner*—Raymond Covington
(74) *Attorney, Agent, or Firm*—Marcelo K. Sarkis; Ivor M. Hughes; Neil H. Hughes

(57) ABSTRACT

A process is provided for the preparation of compounds of formula I,

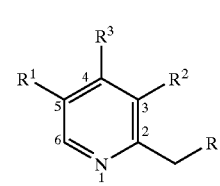

useful in the preparation of compounds such as Omeprazole, Lansoprazole and Pantoprazole, wherein $R^1$=H or $CH_3$, $R^2$=H or $CH_3$, $R^3$=Alkoxy (1–4C), $OCH_2CF_3$, Cyano, Hydrogen, Halogen, Acetoxy or Aryloxy, any electron withdrawing group or salts (organic or inorganic) of electron donating groups, R=Alkoxy, Hydroxy, Halogen, Activated ester, Tosylate, Mesylate, Thiol or Xanthyl, wherein the process for the preparation of compound of formula I employs a free radical reaction to functionalize the 2-position.

7 Claims, No Drawings

OTHER PUBLICATIONS

Yoon, N.M., et al., "Selective Reductions. XIX. The Rapid Reaction of Carboxylic Acids with Borane–Tetrahydrofuran. A Remarkably Convenient Procedure for the Selective Conversion of Carboxylic Acids to the Corresponding Alcohols in the Presence of Other Functional Groups", *J. Org. Chem.*, 1973, vol. 38, pp. 2786–2791.

Chou, S.Y., et al., "Synthesis of 2—Hydroxymethyl–3, 5–Dimethyl–4–Methoxypyridine: A Key Intermediate for Omeprazole", *Heterocylces*, vol. 45, No. 1, 1997, pp. 77–85.

Kohl, B., et al., "AATPase Inhibiting 2–[(2–Pyridylmethyl)sulfinyl]benzimidazoles. 4.[1] A Novel Series of Dimethoxypyridyl–Substituted Inhibitors with Enhanced Selectivity. The Selection of Pantoprazole as a Clinical Candidate", *J. Med. Chem.* 1992, 35, pp. 1049–1057.

Weidmann, K. et al., 2–[(2–Pyridylmethyl)sulfinyl]–1H–thieno[3,4–d]imdazoles. A Novel Class of Gastric H+/K+–ATPase Inhibitors, *J. Med. Chem.*, 1992, 35, 438–450.

Bernardi, R., et al., "Nucleophilic Character of Carbon Free Radicals. A New Convenient, Selective Carboxylation of Heteroaromatic Bases", *Tetrahedron Letters No. 9*, 1973, pp. 645–648.

Minisci, F., et al., "Recent Developments of Free–Radical Substitutions of Heteroaromatic Bases", *Heterocycles*, vol. 28, No. 1, 1989, pp. 489–519.

Minisci, F., "Novel Applications of Free–Radical Reactions in Preparative Organic Chemistry", *Synthesis*, Jan. 1973, pp. 1–24.

Minisci, "Novel Applications of Free–Radical Reactions in Preparative Organic Chemistry", *Synthesis*, No. 1, 1973, pp. 1–24.

Bernardi et al., "Nucleophilic character of carbon free radicals. A new convenient, selective carboxylation of heteroaromatic bases.", *Tetrahedron Letters*, vol. 9, 1973, pp. 645–648.

Fontana, et al., "Homolytic acylation of protonated pyridines and pyrazines with alpha–keto acids: the problem of monoacylation", *J. Org. Chem.*, vol. 56, 1991, pp. 2866–2869.

Citterio, et al., "Nucleophilic character of the alkyl radicals. 19. Absolute rate constants in the homolytic alkylation of protonated heteroaromatic bases by n–butyl and tert.–butyl radicals.", *J. Org. Chem.*, vol. 45, 1980, pp. 4752–4757.

Chou, et al., "Synthesis of 2–hydroxymethyl–3, 5–dimethyl–4–methoxypyridine: a key intermediate for omeprazole", *Heterocycles*, vol. 45, No. 1, 1997, pp. 77–85.

Chemical Abstracts, vol. 51, No. 12, Jun. 25, 1957, Columbus, Ohio, US; Jerchel, et al., "Synthesis with pyridylpyridium halides . . . ", col. 8737.

Epsztajn, et al., "Application of Organolithium and Related Reagents in Synthesis. Part 9[1],. Synthesis and Metallation of 4–Chloropicolin–and 2–Chloroisonicotin–Anilides. A Useful Method for Preparation of 2,3,4–Trisubstituted Pyridines", *Tetrahedron*, vol. 47, No. 9, 1991, pp. 1697–1706.

Epsztajn, et al., "Application of Organolithium and Related Reagents in Synthesis. Part 7[1],. Synthesis and Metallation of 4–Methoxypicolin–and 2–Methoxyisonicotin–Anilides. A Useful Method for Preparation of 2,3,4–Trisubstituted Pyridines", *Tetrahedron*, vol. 45, No. 23, 1989, pp. 7469–7476.

Chu, et al., "Toward the Design of an RNA:DNA Hybrid Binding Agent", *J. Am. Chem. Soc.*, vol. 116, 1994, pp. 2243–2253.

Godard, et al., "Synthesis of new substituted quinolizidines as potential inhibitors of ergosterol biosynthesis", *Tetrahedron*, vol. 51, No. 11, 1995, pp. 3247–3264.

SYNTHESIS OF PHARMACEUTICALLY USEFUL PYRIDINE DERIVATIVES

This application is a continuation-in-part of Ser. No. 09/063,001 field Apr. 21, 1998, now U.S. Pat. No. 6,121,454.

FIELD OF INVENTION

This invention relates to the manufacture of intermediates suitable for use in the manufacture of Omeprazole and other medicines and the use thereof to manufacture Omeprazole and other medicines. This invention in its broadest aspects is directed to the manufacture of intermediates useful in the manufacture of medicines such as Omeprazole, Pantoprazole, and Lansoprazole, intermediates suitable for the use to manufacture medicines and the processes for manufacturing the intermediates and for using those intermediates to manufacture medicines.

BACKGROUND OF INVENTION

The reported synthesis of Omeprazole basically involves the coupling of intermediates A and B to form intermediate C which is oxidized to the sulfinyl or sulfoxy compound, Omeprazole.

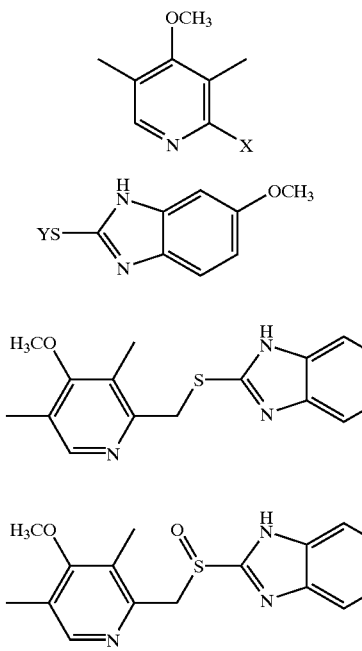

(See for example Canadian Letters Patent No. 1,127,158 Hassle)

Hassle used the N-oxide form of intermediate A:

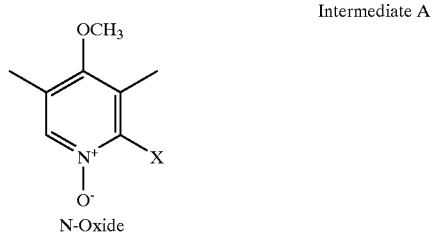

Intermediate A N-Oxide (See Canadian Letters Patent No. 1,234,118)

The N-Oxide form may be considered necessary to prepare the precursor 4-nitro compound and it is essential for the alkylation/functionalization of the 2-position (X), according to Hassle's process. Intermediate A (N-Deoxygenated) is then coupled with intermediate B on the route to Omeprazole.

Esteve, on the other hand, described a synthesis that involves coupling the N-oxides of the 4-nitro or the 4-Chloro with intermediate B to form the N-Oxide of intermediate C. Following that, Esteve either substituted at the pyridinyl 4-position with the methoxy and then reduced the N-Oxide or vice-versa.

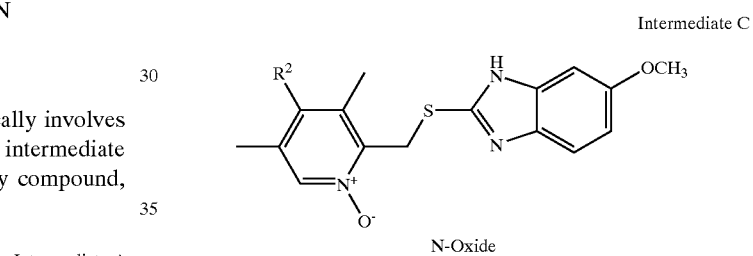

Intermediate C N-Oxide $R^2$: —Cl, —NO$_2$, or —OCH$_3$ (See European Patent No. 484,265)

Torcan, reported a method that offers advantages involving the oxidation and the purification of the final product. Their method comprises oxidizing the amide of Intermediate C to the corresponding amide sulfinyl compound followed by hydrolysis and decarboxylation to form Omeprazole. Torcan did not report processes for the manufacture of the pyridinyl moiety.

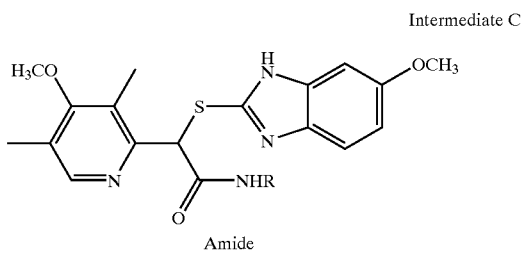

Intermediate C Amide (See U.S. Pat. No. 5,374,730)

Other Oxidation methods used for converting the thioether "Intermediate C" to the sulfinyl are purportedly taught by recent Takeda (CA 1,263,119) and Hassle's (U.S. Pat. No. 5,386,032) patents.

C. L. Pharma's U.S. Pat. No. 5,066,810 teaches a process to manufacture

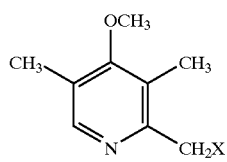

where X is OH or Cl by catalytic hydrogenation of 3,5-dimethyl-4-methoxy-2-cyanopyridine as depicted below

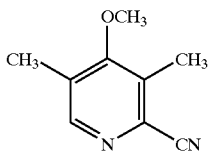

in the presence of an inert diluent, the resulting 3,5-dimethyl-4-methoxy-2-aminomethylpyridine as depicted below

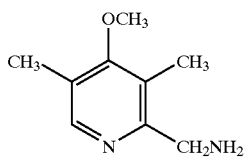

which is then reacted with sodium nitrite in aqueous-acidic solution to give 3,5-dimethyl-4-methoxy-2-hydroxymethylpyridine and ultimately reacting the latter with thionyl chloride to give 3,5-dimethyl-4-methoxy-2-chloromethylpyridine.

In European Patent Publication No. 0103553 and in Canadian Letters Patent 1,234,118 and in U.S. Pat. Nos. 4,544,750 and 4,620,008, the following synthetic route for the pyridine part of omeprazole is described:

Scheme I

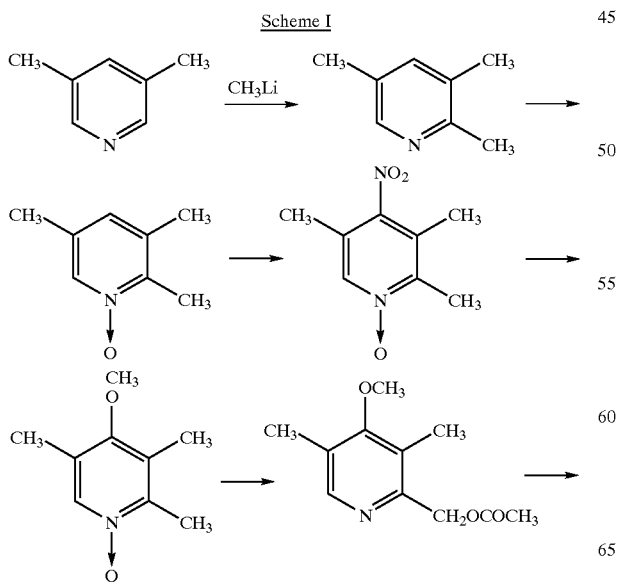

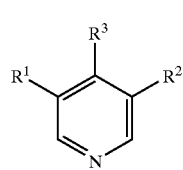

More recently, a method for the synthesis of intermediate A was published by a Taiwanese group. This procedure consisted of preparation of the pyrone, pyridone and pyridine derivatives that can be converted to intermediate A. (Heterocycles, 45, 1997, 77).

There are certain disadvantages associated with the current manufacturing processes, largely derived from the N-Oxide intermediates. Nitropyridines and their N-oxides are suspected carcinogens and therefore are unsafe to handle. Also, the above processes employ the nitropyridines and their N-oxides in the early or late stages of the manufacture. In both cases the suspected carcinogens are potential impurities.

While the Taiwanese method does not employ nitropyridines or N-oxides, it suffers from the disadvantage that it employs a large number of steps (approximately 10 steps) and the low availability of the starting material. Both are factors that affect the manufacturing yield and cost.

It is therefore an object of the invention to provide a method of manufacturing intermediates useful in preparing medicines where said intermediates avoid N-oxides that are suspected carcinogens.

It is also another object of the invention to provide methods of manufacturing intermediates useful in preparing medicines where said method employs intermediates that are safe to handle.

It is also another object of the invention to provide methods of manufacturing intermediates useful in preparing medicines wherein the number of steps are minimal in number.

It is also another object of the invention to provide methods of manufacture which incorporate materials that are readily available.

Further and other objects of the invention will be realized by those skilled in the art from the following summary of the invention.

SUMMARY OF THE INVENTION

According to one aspect of the invention, there is provided a process of making Compound III (shown hereafter) by reacting a compound of the formula II

II with an organic free radical .$R^4$ (for example prepared in situ) to produce the compound of formula III

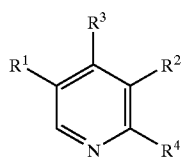

wherein

R¹=H or CH₃

R²=H or CH₃

R³=Alkoxy (1–4C), OCH₂CF₃, Cyano, Hydrogen, Halogen, Acetoxy or Aryloxy, any electron withdrawing group or salts (organic or inorganic) of electron donating groups R⁴=Alkyl, Acyl (ketone), Amides (carbamoyl), Alkoxycarbonyl (COOR¹, R¹=(1–3C)), Aryloxycarbonyl, Carboxylic Acid, Aryloxymethyl (—CH₂OAr), Phenoxymethyl, Hydroxymethyl (—CH₂OH)

or an obvious chemical equivalent. (The source of R⁴ may be any suitable compound.)

According to another aspect of the invention, there is provided a process of producing a compound of formula I'

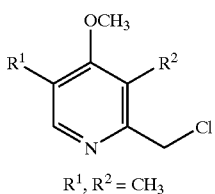

using intermediate III. An exemplary process may be by carrying out the following reaction step or steps which are obvious chemical equivalents of the following steps:

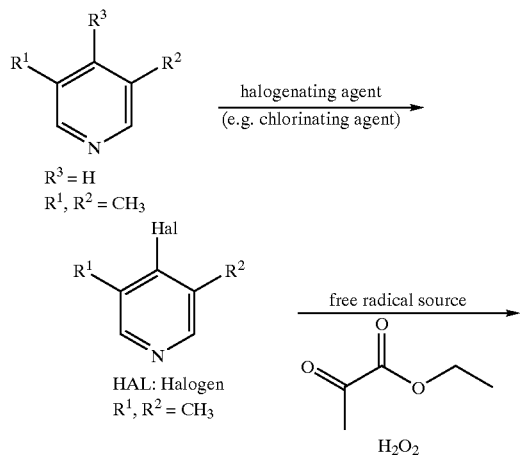

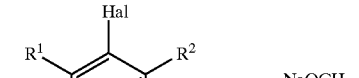

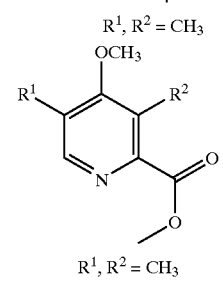

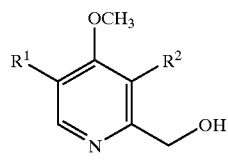

According to another aspect of the invention, there is provided a process of manufacturing Omeprazole by using the intermediate formed by the process above described with the appropriate substituents or an obvious chemical equivalent.

According to another aspect of the invention, there is provided a process of manufacturing Pantoprazole by using the intermediate formed by the process above described with the appropriate substituents or an obvious chemical equivalent.

According to another aspect of the invention, there is provided a process of manufacturing Lansoprazole by using the intermediate formed by the process above described with the appropriate substituents or an obvious chemical equivalent.

According to another aspect of the invention, there is provided a process of forming a compound having the structure

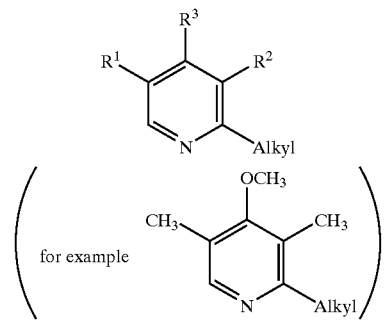

by reacting a compound having the structure

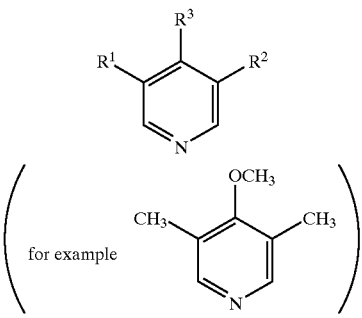

$R^1$, $R^2$ and $R^3$ as previously defined, with a radical .alkyl under free radical reaction conditions or an obvious chemical equivalent.

According to another aspect of the invention, there is provided a process of forming a compound having the structure

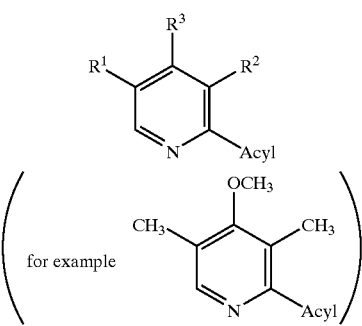

by reacting a compound having the structure

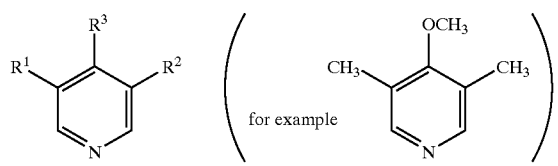

$R^1$, $R^2$ and $R^3$ as previously defined, with a radical .acyl under free radical reaction conditions or obvious chemical equivalent.

According to another aspect of the invention, there is provided a process of forming a compound having the structure

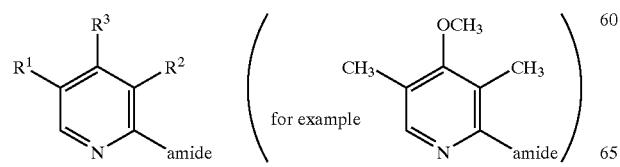

by reacting a compound having the structure

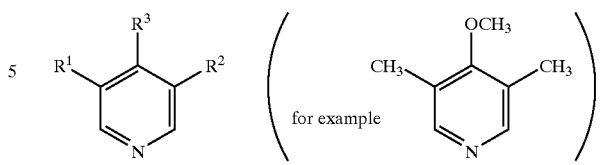

$R^1$, $R^2$ and $R^3$ as previously defined, with a radical .amide under free radical reaction conditions or obvious chemical equivalent.

According to another aspect of the invention, there is provided a process of forming a compound having the structure

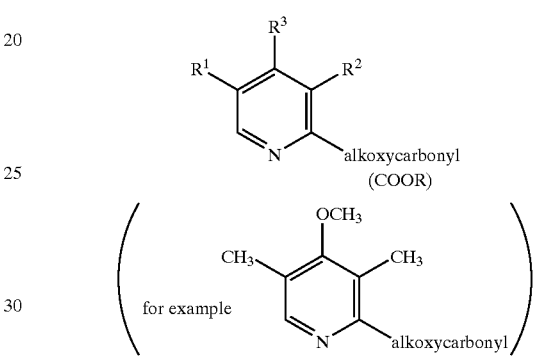

by reacting a compound having the structure

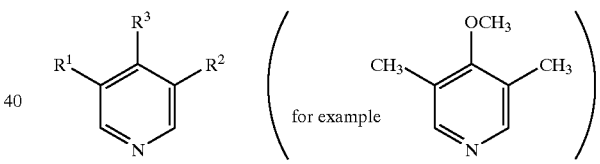

$R^1$, $R^2$ and $R^3$ as previously defined, with a radical .alkoxycarbonyl under free radical reaction conditions or obvious chemical equivalent.

According to another aspect of the invention, there is provided a process of forming a compound having the structure

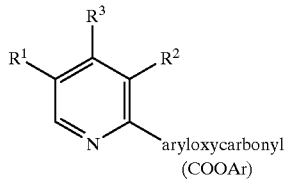

by reacting a compound having the structure

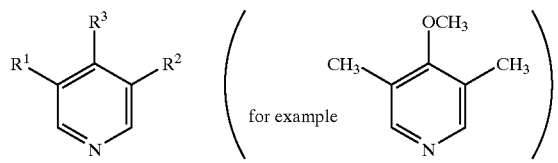

$R^1$, $R^2$ and $R^3$ as previously defined, with a radical .aryloxycarbonyl under free radical reaction conditions or obvious chemical equivalent.

According to another aspect of the invention, there is provided a process of forming a compound having the structure

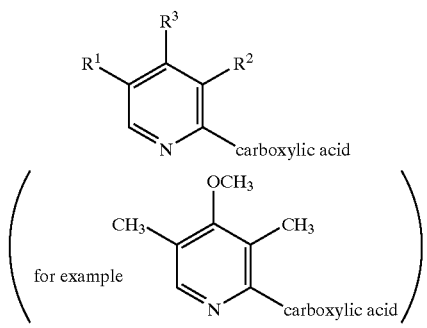

by reacting a compound having the structure

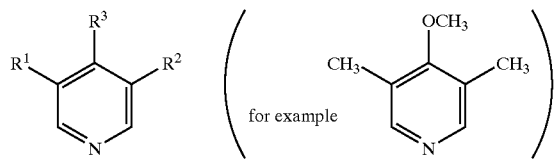

$R^1$, $R^2$ and $R^3$ as previously defined, with a radical .carboxylic acid under free radical reaction conditions or obvious chemical equivalent.

According to another aspect of the invention, there is provided a process of forming a compound having the structure

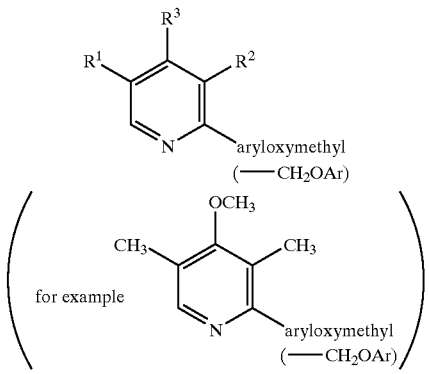

by reacting a compound having the structure

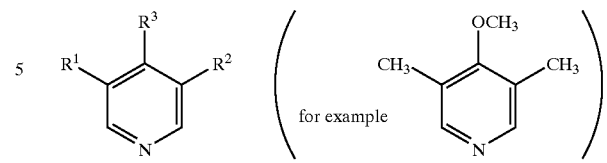

$R^1$, $R^2$ and $R^3$ as previously defined, with a radical .aryloxymethyl (for example, .phenoxymethyl) under free radical reaction conditions or obvious chemical equivalent.

According to another aspect of the invention, there is provided a process of forming a compound having the structure

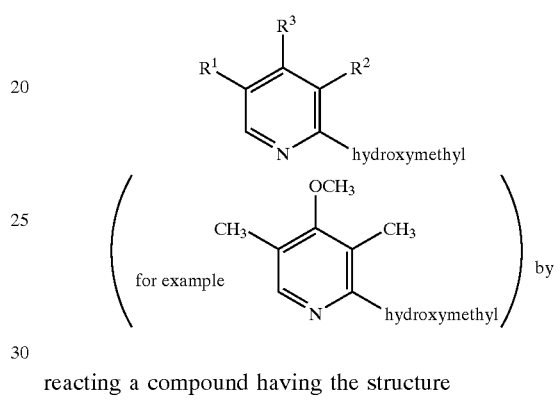

reacting a compound having the structure

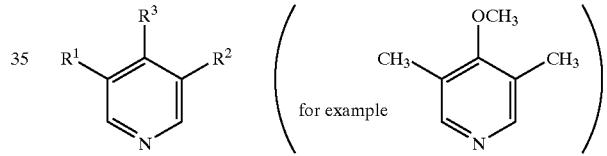

$R^1$, $R^2$ and $R^3$ as previously defined, with a radical .hydroxymethyl under free radical reaction conditions or obvious chemical equivalent.

The inventors propose that their approach would be highly suitable for use to make pyridines which are intermediates that could be used to make medicines.

Applicants propose as exemplary of their invention that the following pyridine compound:

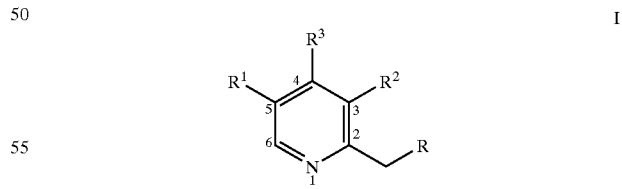

wherein
  $R^1$=H or $CH_3$
  $R^2$=H or $CH_3$
  $R^3$=Alkoxy (1–4C), $OCH_2CF_3$, Cyano, Hydrogen, Halogen, Acetoxy or Aryloxy, any electron withdrawing group or salts (organic or inorganic) of electron donating groups
  R=Alkoxy, Hydroxy, Halogen, Activated ester, Tosylate, Mesylate, Thiol, or Xanthyl be prepared by the following schemes of reaction (in suitable solvents):

Scheme 1

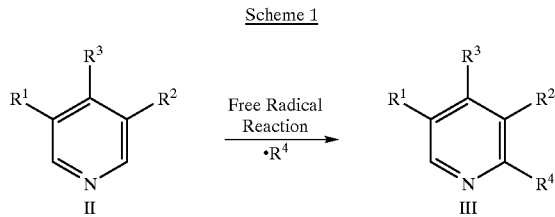

wherein formula II or III:
$R^1$, $R^2$, $R^3$ are the same as specified in formula I
$R^4$=Alkyl, Acyl (ketone), Amides (carbamoyl), Alkoxycarbonyl (COOR', R'=(1–3C)), Aryloxycarbonyl, Carboxylic acid, Aryloxymethyl, Hydroxymethyl.

Compound I may then be manufactured using intermediate III.

For the synthesis of an intermediate useful in the manufacture of Omeprazole, the following substituents appear on the intermediate of formula I' where $R^1=R^2=CH_3$; $R^3=OCH_3$, R=Cl. An exemplary process of manufacture may be characterized by the steps in Scheme 2A.

a) Functionalization of the 4-Position: (Step 01 in Scheme 2A)

Reacting a compound of the formula II, where $R^3$=H with a halogenating agent, examples include and are not limited to thionyl halide, phosphorous oxyhalide, or phosphorous pentahalide.

This reaction could be carried out in an inert solvent such as toluene, dimethylbenzene, chlorobenzene or could be carried out neat with no solvent, with the halogenating reagent used in excess (2–5 eq.), to be the solvent. The mode of addition of reagents is not important, i.e. pyridine to the halogenating reagent or the halogenating reagent to pyridine. The addition is done dropwise, under nitrogen, at a temperature range of 0–70° C. At the end of the reaction the product is obtained as a salt. The free base could be obtained by typical procedures known to a person skilled in the art.

b) Functionalization of the 2-Position: (Step 02 in Scheme 2A)

Reacting the 4-halopyridine with an organic free radical comprised of the $R^4$ groups specified above, preferably the alkoxycarbonyl. Several alkoxycarbonyl radical sources can be used: (see e.g. *Tet. Lett.* 1973, 645).

For Example;
i. Redox decomposition of oxyhydroperoxides of α-ketoesters (Scheme-2),
ii. Oxidative decarboxylation of semiesters of oxalic acid by peroxydisulfate or lead tetraacetate,
iii. Hydrogen abstraction from alkyl formates.

Method in subparagraph (i) is preferred method because it provides simple conditions and good yields. The pyridine used in this reaction could be in the free base or the salt form.

The salt could be prepared prior to the reaction or formed in situ and it is the result of reacting the pyridine with an organic or inorganic acid, preferably sulfuric acid. An inert solvent such as Toluene or Xylene could be added to form a two-phase reaction. If an organic solvent is added, it is preferable in a volume equal to or higher than that of water. In parallel, in another flask the reagent required to functionalize the 2-position on the pyridine moiety, such as the pyruvate (C1–C3) (0.9–3.0 eq.) is cooled to about –10° C. and hydrogen peroxide (0.9–3.0 eq.) is added dropwise. This solution and a solution of Iron sulfate heptahydrate (0.9–3.0 eq.) in water are, slowly and simultaneously, added to the pyridine solution which is stirred at 0–5° C.

c) Reduction of the $R^4$ Group: (Step 03 in Scheme 2A)

Reacting the group on the 2-position with an appropriate reducing agent to prepare a compound of the formula I, where R corresponds to an OH group. For example, 2-alkoxycarbonyl-4-Halopyridine could be reacted with an appropriate reagent to effect reduction of the ester moiety to an alcohol. Reducing agents such as Diisobutylaluminum Hydride (e.g. *Syn* 1975, 617) in an appropriate solvent such as toluene, tetrahydrofuran, hexane or a combination of those solvents could be used. Also, sodium bis[2-methoxyethoxy]aluminum hydride (e.g. *J. Heterocyclic chem.,* 1990; 27, 2125; *Syn.,* 1976, 526), borohydrides, such as Sodium or Lithium borohydride, (e.g. *J. Org. Chem.* 1963, 28, 3261; *Tet.* 1979, 35, 567;) could be used in a variety of protic solvents such as methanol, ethanol, isopropanol, water, a combination of those solvents and aprotic solvents such as toluene, xylene, ethers or a combination of protic and aprotic solvents. The reduction could be performed by typical procedures known to a person skilled in the art.

d) Nucleophilic Substitution of the Halogen on the 4-Position by an —$OCH_3$ Radical: (Step 04 in Scheme 2A)

Nucleophilic substitution of the halogen on the 4-position by a nucleophile such as a —$OCH_3$ radical can be performed using methoxide salts such as sodium, potassium or copper methoxide (e.g. see *Chem & Ind.,* 1967, 1784). Also, sodium or potassium methoxide could be used in the presence of a copper salt such as cuprous iodide, cuprous bromide or cuprous chloride. The reaction can be carried out in an inert solvent such as dimethylformamide, dimethylacetamide, dimethylsufoxide, diglyme, methanol, or a combination of those solvents. The methoxide salt is used in excess (2–7 eq.) and the reaction temperature could be between 65° C. and reflux.

e) Nucleophilic Substitution of the OH Radical by a Halogen

The conversion of the hydroxymethyl moiety on the 2-position to a halomethyl, for example, chloromethyl could be achieved by employing methods known to a person skilled in the art, e.g. using thionyl chloride in an inert solvent such as dichloromethane, toluene, xylene.

Scheme 2A

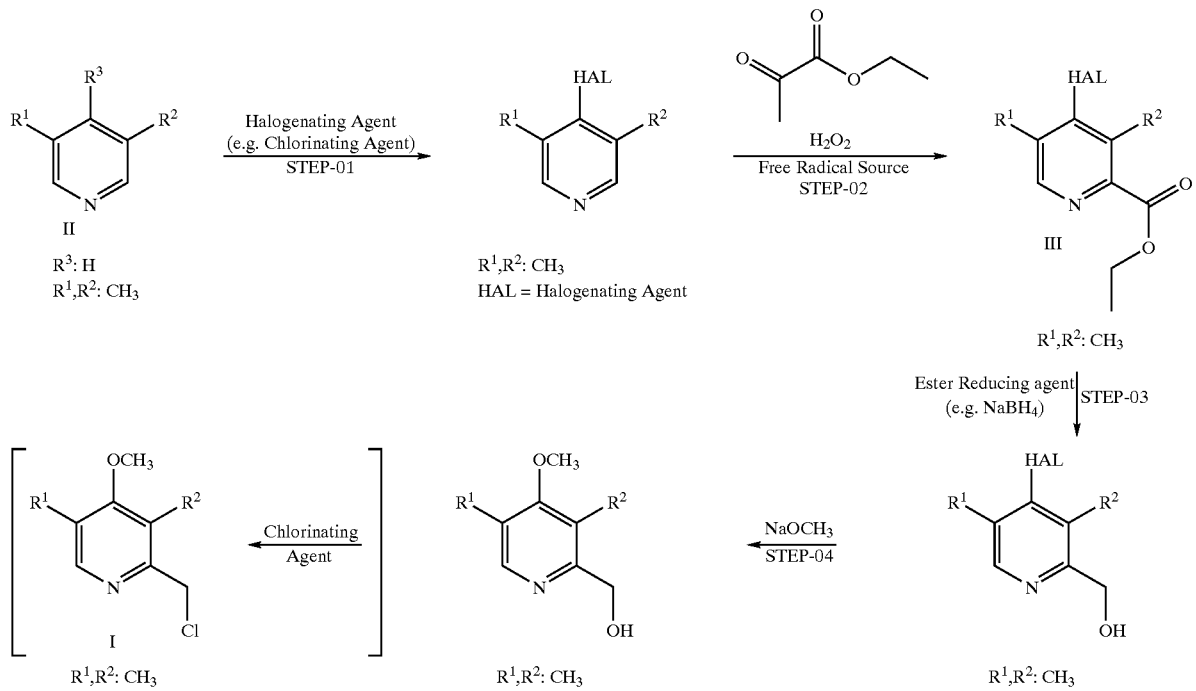

For making an intermediate suitable to make omeprazole, the following process may be carried out:

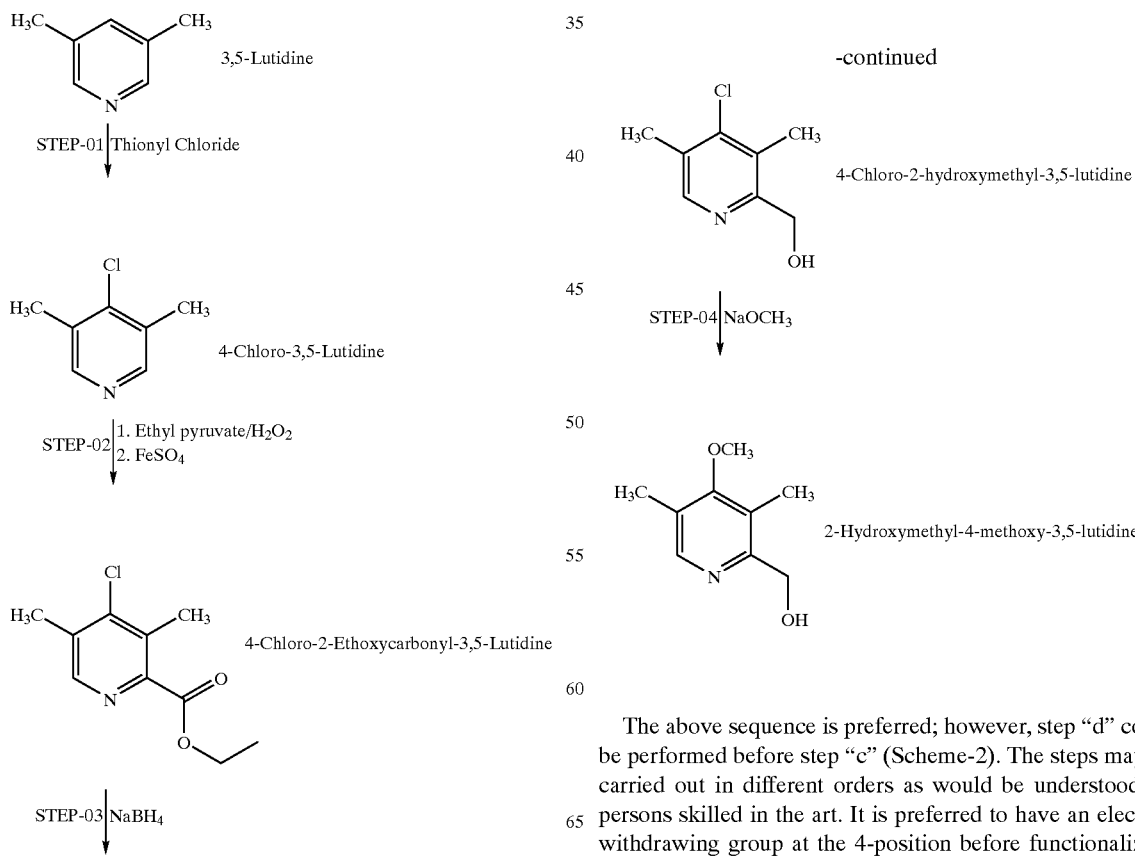

The above sequence is preferred; however, step "d" could be performed before step "c" (Scheme-2). The steps may be carried out in different orders as would be understood by persons skilled in the art. It is preferred to have an electron withdrawing group at the 4-position before functionalizing the 2-position.

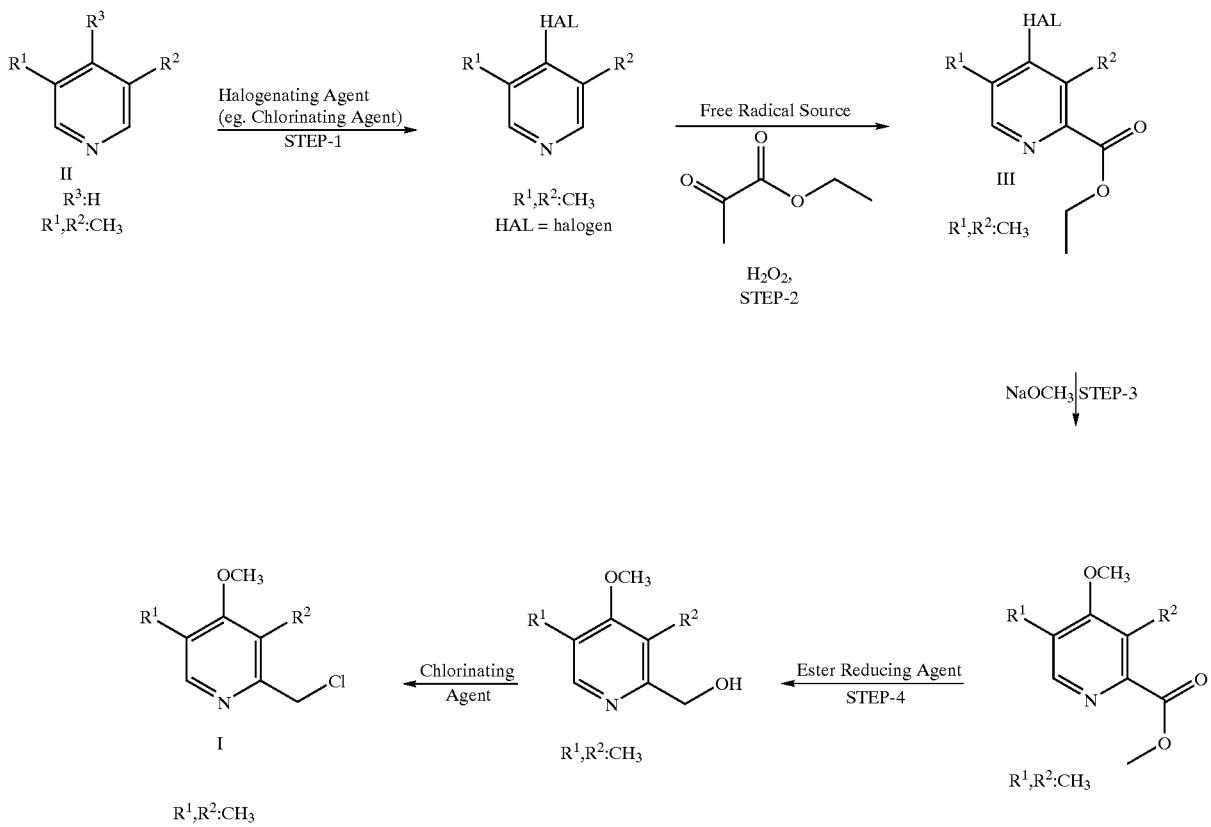

Scheme 2

Furthermore, the unreacted starting material in the free radical reaction could easily be recovered by alkaline treatment and extraction with an organic solvent. The 2-alkoxycarbonyl product is obtained in purity higher or equal to 90%. Analytically pure product could be obtained by hydrolysis of the ester to the acid according to methodologies generally known in the art. For example, the hydrolysis of III to the acid (IV) (see Scheme 3) could be accomplished using aqueous sodium hydroxide or aqueous hydrochloric acid. The acid obtained (IV) could then be converted back to the ester using methods generally known in the art. For example, reaction of the acid with thionyl chloride followed by an alcohol such as methanol. On the other hand, the acid could be reduced directly to the alcohol using carboxylic acid reducing agents that are generally known to persons skilled in the art. For example, Diborane, diborane complexes (e.g. *Syn.* 1979, 704; *J. Org. Chem.* 1973, 38, 2786), lithium aluminum hydride, diisobutylaluminum hydride, sodium borohydride, lithium borohydride; these reagents can be used pure or with catalysts and additives (e.g. *J. Org. Chem.* 1982, 47, 4702; *Tet.* 1992, 48, 4623).

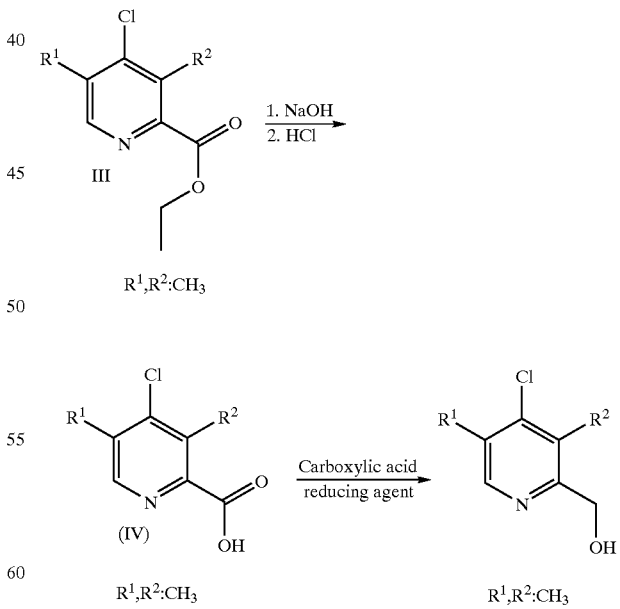

Scheme 3

While the reaction involving the nucleophilic substitution of the 4-halo substituent generally goes to completion, an ether cleavage product (V) is also usually formed. This product could be recovered from the aqueous layer and treated with an alkylating agent to get the 4-alkoxy product. This 4-nucleophilic substitution reaction can be geared to provide the ether cleavage product, such as (V) and (VI), as the major products. This could be achieved by, for example, employing longer reaction times (over 15 hours). The synthesis of 4-hydroxy products such as compounds (V) and (VI) is also within the scope of this invention. These products are inorganic salts of 4-hydroxypyridines. The 4-hydroxypyridines may also take the form of these organic salts. Compound (V) may be a mono organic/inorganic salt. Compound (VI) may be a mono- or di-organic/inorganic salt (such as the sodium or potassium salt).

The alkylation of the 4-hydroxy compounds could be accomplished employing methods that are generally known to a person skilled in the art. For example, compounds (V) or (VI) could be methylated by treatment with 1 equivalent (for compound V) or 2–5 equivalents (for compound VI) of a methylating agent such as Iodomethane, in an inert aprotic solvent such as dimethylformamide.

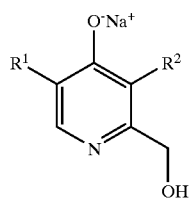

(V)

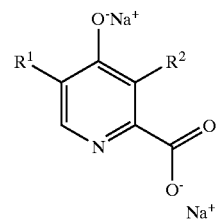

(VI)

According to another aspect of the invention, there is provided a process of reacting a compound of formula II

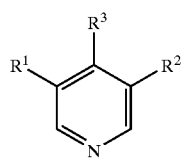

II wherein $R^1$=H or $CH_3$ $R^2$=H or $CH_3$ $R^3$ is hydrogen with $SOCl_2$ or any other halogenating agent to form 4-halopyridine derivatives.

In one embodiment the halogenating agent can be used neat, and in another embodiment it can be used in the presence of solvents such as toluene, xylene, chlorobenzene or any other suitable inert solvent. Preferably the reaction occurs substantially solvent free.

The following is a list of the substituents R, $R^2$, $R^3$, $R^4$, $R^5$, on Formula I, that correspond to the substituents on the medicines:

| $R^1$ | $R^2$ | R | $R^3$ | Precursor for |
|---|---|---|---|---|
| $CH_3$ | $CH_3$ | 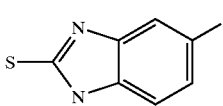 | $OCH_3$ | Omeprazole |
| H | $OCH_3$ | 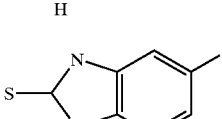 | $OCH_3$ | Pantoprazole |
| H | $CH_3$ | 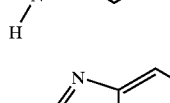 | $OCH_2CF_3$ | Lansoprazole |

19

The invention will now be illustrated with reference to the following examples of manufacture:

EXAMPLE 1

Synthesis of 4-Chloro-3,5-dimethylpyridine 3,5-Dimethylpyridine (1 eq.) was added dropwise to thionyl chloride (1–5 eq.); either neat or in a solvent (2–10 volumes), (such as toluene, 4-chlorobenzene, xylene etc.) at a temperature ranging frown 0–70° C. At the end of the addition the mixture was heated to reflux for 12–20 hours. At the end of the reaction the solvent (1–5 volumes) was added (if not already present). A fraction of the solvent was distilled to get rid of the excess thionyl chloride. The precipitated solid was filtered, washed with toluene followed by methanol, a brown solid was obtained. The crude product was dissolved in hot methanol, treated with charcoal, filtered over celite, cooled to room temperature and then to 0–5° C. and allowed to crystallize. 4-Chloro-3,5-dimethyl pyridine.HCl was obtained in over 70% yields.

Another work-up method: At the end of the reaction, the mixture was allowed to cool down to room temperature and an organic solvent such as toluene (1–5 vol.) was added (if not already present), followed by dropwise addition of an aqueous NaOH solution until pH=9–11. The phases were separated and the toluene was evaporated to produce 4-Chloro-3,5-dimethylpyridine in the free base form.

Also, the mode of addition could be reversed with no effect on the yield, i.e., thionyl chloride addition to 3,5-dimethylpyridine.

EXAMPLE 2

Synthesis of 2-Pyridinecarboxylic acid, 4-chloro-3,5-dimethyl-, ethyl ester

Ethyl pyruvate (0.9–3 eq.) was stirred and cooled (−20–+0° C.) and hydrogen peroxide (30–35%, 0.9–3 eq) was added dropwise. This solution and a solution of Iron sulfate heptahydrate (0.9–3 eq.) in water (1–5 vol.) were then slowly and simultaneously added dropwise into a stirred solution of 4-Chloropyridine (1 eq) in water (1–5 vol.) and conc. $H_2SO_4$ (1–4 eq.) and Toluene (0–20 vol.), keeping the temperature below 25° C. The mixture was then stirred at room temperature until the reaction is judged complete. The mixture was poured into ice cold NaOH (10%) solution. Toluene (2–5 vol.) was added (If not already present), the layers were separated. The toluene layer was washed with 0.5N HCl solution and evaporated to yield the crude 2-Pyridinecarboxylic acid, 4-chloro-3,5-dimethyl-, ethyl ester in over 90% yield based on the consumed starting material and over 50% isolated yield.

The starting material present in the aqueous layer was free based and recycled.

EXAMPLE 3

Pyridinecarboxylic acid, 3,5-dimethyl-4-methoxy-, methyl ester

A solution of the crude Pyridinecarboxylic acid, 4-chloro-3,5-dimethyl-, ethyl ester (1 eq.) in methanol (3–10 vol.) was added freshly prepared sodium methoxide (2–5 eq.). The mixture was heated under reflux for 5–12 hours. Methanol was evaporated and substituted with toluene. Water was added and the layers were separated. Toluene was evaporated to yield the crude Pyridinecarboxylic acid, 3,5-dimethyl-4-methoxy-, methyl ester in over 75% yield.

20

EXAMPLE 4

3,5-dimethyl-2-hydroxymethyl-4-methoxypyridine

The crude Pyridinecarboxylic acid, 3,5-dimethyl-4-methoxy-, methyl ester (1 eq.) was dissolved in toluene (3–10 vol.). The solution was stirred under a nitrogen atmosphere and diisobutylaluminum hydride (neat or in toluene) (2–3 eq.) was added dropwise keeping the temperature between (+10 to−+25° C.). At the end of the addition the reaction was stirred at room temperature for 30 minutes and then it was heated to 50–60° C.1 hour, or until the reaction was judged complete. At the end of the reaction the excess diisobutylaluminum hydride was quenched with ethyl acetate. An aqueous base solution (such as 20% NaOH) was added and the layers were separated. The toluene layer was evaporated to yield the crude 3,5-dimethyl-2-hydroxymethyl-4-methoxypyridine in over 85% yield.

EXAMPLE 5

Synthesis of 4-Chloro-3,5-Lutidine

Thionyl chloride was loaded into a reaction vessel equipped with a stirrer, a condenser, a dropping funnel, and a nitrogen bubbler. The temperature was lowered to 0–5° C. and 3,5-lutidine was added dropwise, keeping the temperature between 0 and 10° C. When the addition was complete the reaction mixture was refluxed for 18 hours. The mixture was cooled to 65° C. and toluene (4 volumes) were added. 1.5 volumes of the mixture were distilled under vacuum. The heavy brown precipitate was collected by filtration. The crude product was recrystallized from methanol (3 volumes). Filtration afforded the product, 4-Chloro-3,5-Lutidine, as a beige solid, this was washed with methanol and dried under vacuum at 40° C.; yield: 75%.

EXAMPLE 6

Synthesis of 4-Chloro-2-Ethoxycarbonyl-3,5-Lutidine

4-Chloro-3,5-Lutidine (1 eq.) was suspended in DI-water (0.5 volumes) in a 3-neck round bottom flask. While cooling in an ice bath, concentrated sulfuric acid (0.5 eq.) was added dropwise. Toluene (4.5 volumes) was added and the mixture was cooled in an ice bath to 0–5° C. In another round bottom flask Ethyl pyruvate (1.05 eq.) was cooled to −10° C. and hydrogen peroxide (1 eq.) was added dropwise to form a cloudy solution. After addition the mixture was further stirred for 15 minutes at −10° C. In another flask, Iron (II) sulfate heptahydrate (1 eq.) was dissolved in DI-water (2 volumes (based on Iron sulfate)).

The oxyhydroperoxide solution and the Iron sulfate solution were added dropwise and simultaneously to the lutidine salt solution. The temperature was maintained at 0–5° C. When the addition was finished, the mixture was further stirred for 30 minutes at 0–5° C. The toluene layer was separated and washed with HCl (0.5 M, 53 mL). The combined organic extracts were dried over sodium sulfate, filtered and evaporated to yield a yellow oil in 35% yield.

Recovery of Un-reacted Starting Material

The aqueous layers were free based with NaOH (30%) and extracted with toluene.

EXAMPLE 7

Synthesis of 4-Chloro-2-hydroxymethyl-3,5-Lutidine

4-Chloro-2-ethoxycarbonyl-3,5-Lutidine (1 equivalent) was dissolved in methanol (4 volumes). The solution was cooled in an ice bath and while stirring sodium borohydride (1–4 eq.) was added in portions. The mixture was stirred and heated to reflux (80–85° C.). At the end of the reaction, the solvent was evaporated, water (2 volumes) was added and the product was extracted with toluene (2×4 volumes). The combined organic layers were stirred in an ice bath and HCl gas (1.2 eq.) was bubbled in solution. The 4-Chloro-2-hydroxymethyl-3,5-Lutidine hydrochloride salt was filtered, washed with toluene and dried at 50° C. at high vacuum. The product was obtained as a white solid in 85% yield.

In another work-up method the combined organic extracts were dried over sodium sulfate, filtered, and evaporated to yield the 4-Chloro-2-hydroxymethyl-3,5-Lutidine product as an off white solid; yield 85%.

EXAMPLE 8

Synthesis 2-hydroxymethyl-4-Methoxy-3,5-Lutidine

In a round bottom flask equipped with a stirrer, a condenser and a nitrogen bubbler, 4-Chloro-2-hydroxymethyl-3,5-Lutidine (1 eq.) was dissolved in Dimethylformamide (3–9 volumes) and Methanol (1.5–4.5 volumes). Sodium methoxide (4 eq.) was added and the temperature was raised to (95–100° C.). At the end of the reaction the solvent was distilled under vacuum. Water (2 volumes) was added to the residue and the product was extracted with dichloromethane (2×4 volumes). The combined organic extracts were dried over sodium sulfate, filtered and evaporated. The crude product, 2-hydroxymethyl-4-Methoxy-3,5-lutidine, was obtained in 55% yield.

In another work-up method, after evaporation of the dimethylformamide/methanol, water (2 volumes was added to the residue and the product was extracted with toluene (3×4 volumes). The organic extracts were combined and while cooling and stirring HCl gas (1.2 eq.) was bubbled into solution. The product 2-hydroxymethyl-4-Methoxy-3,5-lutidine hydrochloride salt was filtered and washed with toluene. The crude product was obtained as a white solid in 50% yield.

EXAMPLE 9

Synthesis of 2-carboxy-4-hydroxy-3,5-lutidine

Starting with 2-carboxy-4-chloro-3,5-lutidine, a sodium methoxide nucleophilic substitution reaction was conducted as described above for 24 hours. The aqueous layer was acidified to pH 2.5 with concentrated Hydrochloric acid. The precipitate was filtered and washed with water and dried under vacuum at 50° C. The 2-carboxy-4-hydroxy-3,5-lutidine product was obtained as a light brown solid in 89% yield.

EXAMPLE 10

Synthesis of 4-Methoxy-2-methoxycarbonyl-3,5-Lutidine from 2-carboxy-4-hydroxy-3,5-lutidine Sodium hydride (60%, 2 eq.) was dissolved in dry dimethylformamide (5 volumes) and 2-carboxy-4-hydroxy-3,5-lutidine (1 eq.) was added. The mixture was stirred under a stream of nitrogen for 15 minutes and Iodomethane (2.5 eq.) was added. The mixture was stirred at room temperature for 12 hours. Deionized water was added and the product was extracted three times with dichloromethane. The combined organic extracts were dried over sodium sulfate, filtered and the solvent was evaporated to give the 4-Methoxy-2-methoxycarbonyl-3,5-Lutidine product as a light brown oil in 65% yield.

EXAMPLE 11

Synthesis of 4-Methoxylutidine

Sodium methoxide (2 eq.) was dissolved in methanol (1.5 volumes) and dry dimethylformamide (2 volumes). The solution was heated to (95–100° C.)and while stirring under a stream of nitrogen, 4-chlorolutidine (1 eq.) was added dropwise. At the end of the reaction (about 2 hours), the mixture was cooled in an ice bath and cold water (10 volumes) was added. The product was extracted with dichloromethane (3×2 volumes). The combined organic extracts were dried over sodium sulfate, filtered and the solvent was evaporated under vacuum. Light yellow oil was obtained in 72% yield.

EXAMPLE 12

Synthesis of 2-carboxy-4-chloro-3,5-lutidine

4-Chloro-2-Ethoxycarbonyl-3,5-Lutidine (1 eq.) was suspended in 10% sodium hydroxide aqueous solution (4 eq.), the mixture was stirred and heated to 80° C. After 4 hours a homogeneoussolution was obtained. The solution was washed with toluene and then acidified to pH 2.5. The white precipitate was extracted with dichloromethane (3×5 volumes). The combined organic extracts were dried over sodium sulfate, filtered and the solvent was evaporated under vacuum. The 2-carboxy-4-chloro-3,5-lutidine product was obtained as an off white solid in 85% yield.

EXAMPLE 13

Synthesis of 4-Chloro-2-hydroxymethyl-3,5-Lutidine from 2-carboxy-4-chloro-3,5-lutidine 2-carboxy-4-chloro-3,5-lutidine (1 eq.) was suspended in dry dimethylformamide and $BH_3.THF$ solution (1M in tetrahydrofuran, 3.5 eq.) was added. The mixture was heated to 60° C. and stirred under a nitrogen atmosphere until completion (1.5 hours). The mixture was cooled in an ice bath and $THF/H_2O$ (1:1) mixture (10 volumes) was added slowly. The aqueous layer was saturated with sodium chloride and the tetrahydrofuran layer was separated. The aqueous layer was extracted with ether. The combined organic extracts were dried over sodium sulfate, filtered and the solvent was evaporated under vacuum. The 4-Chloro-2-hydroxymethyl-3,5-Lutidine product was obtained in 51% yield.

Other specific intermediate (I) compounds can be prepared by persons skilled in the art having regard to the teachings herein.

Thus, as many changes can be made to the examples without departing from the scope of the invention, it is intended that all material contained herein be interpreted as illustrative of the invention and not in a limiting sense.

The embodiments of the invention in which an exclusive property or privilege is claimed are as follows:

1. A compound of formula IV

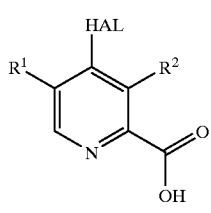

wherein
$R^1, R^2 = CH_3$
HAL=Halogen.

2. The compound

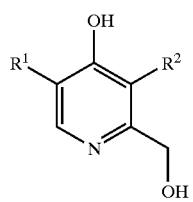

and its inorganic/organic salts, wherein $R^1$ and $R^2$ are selected from lower alkyl.

3. The compound

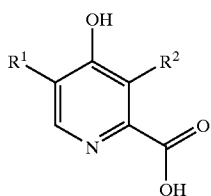

and its mono- and di-inorganic/organic salts, wherein $R^1$ and $R^2$ are selected from lower alkyl.

4. The compound of claim 2 wherein $R^1$ and $R^2$ are each methyl.

5. The compound of claim 3 wherein $R^1$ and $R^2$ are each methyl.

6. A process of reacting

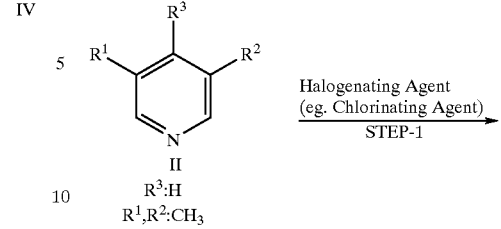

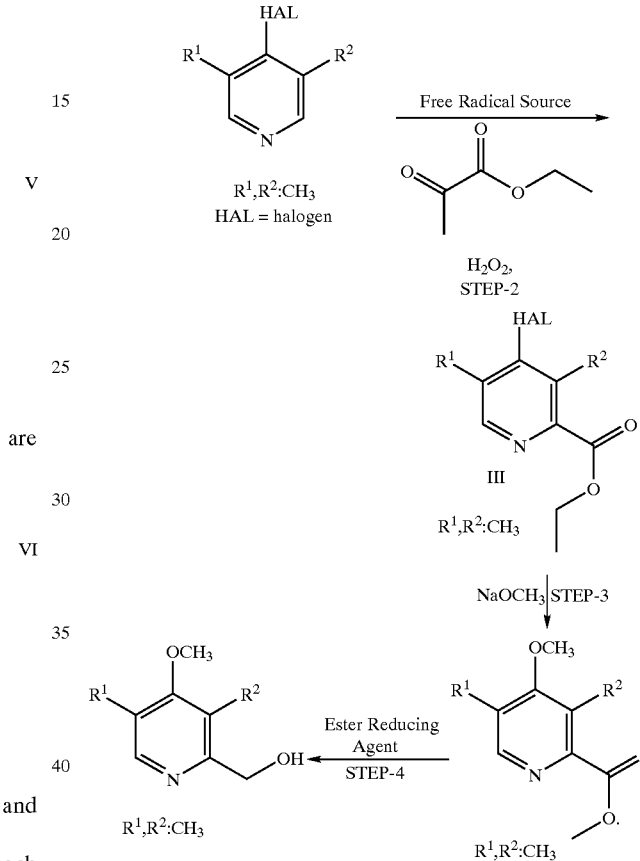

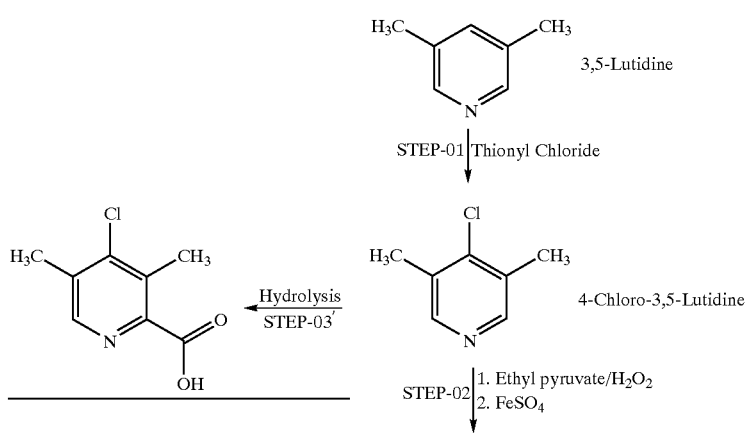

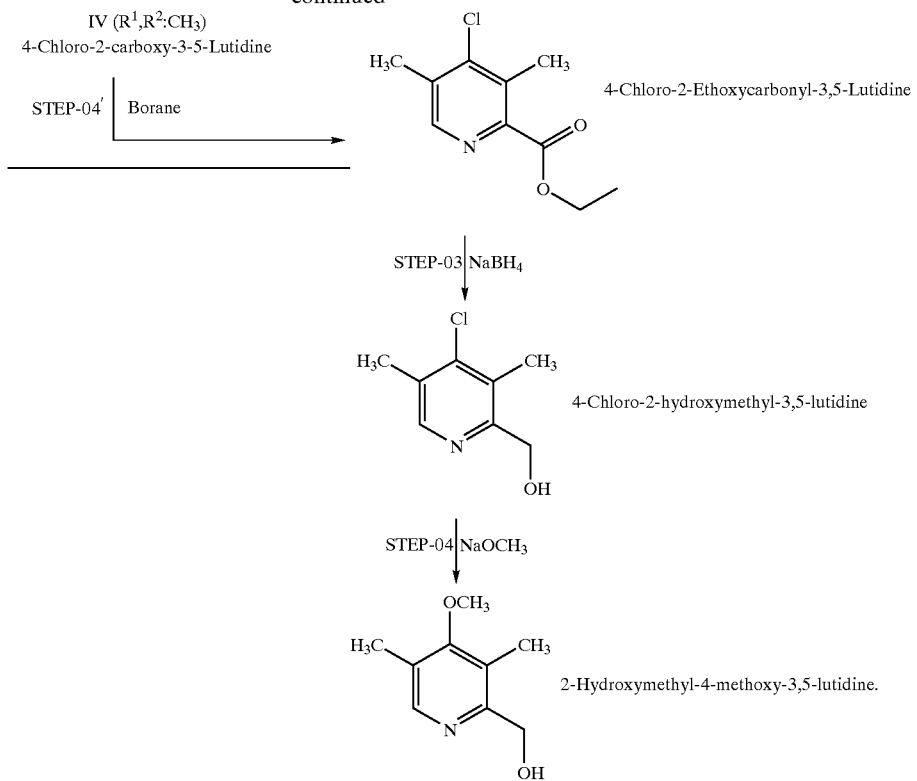

7. A process of reacting